United States Patent [19]

Murr

[11] 4,169,663
[45] Oct. 2, 1979

[54] EYE ATTENTION MONITOR

[75] Inventor: William C. Murr, Piedmont, Calif.

[73] Assignee: Synemed, Inc., Berkeley, Calif.

[21] Appl. No.: 881,794

[22] Filed: Feb. 27, 1978

[51] Int. Cl.² .............................. A61B 3/14; G01J 1/20
[52] U.S. Cl. ...................................... 351/7; 250/203 R
[58] Field of Search ................. 351/7, 6; 250/203, 209

[56] References Cited

U.S. PATENT DOCUMENTS

| 2,724,305 | 11/1955 | Brant | 351/7 |
| 3,583,794 | 6/1971 | Newman | 351/6 |
| 3,724,932 | 4/1973 | Cornsweet et al. | 351/7 |
| 3,864,030 | 2/1975 | Cornsweet | 351/7 |

*Primary Examiner*—John K. Corbin
*Assistant Examiner*—Rodney B. Bovernick

[57] ABSTRACT

A device for monitoring eye attention along an axis includes a telescope directed toward the eye, and a four quadrant photocell detector disposed at the image plane of the telescope. The four photocell outputs are summed to produce X, Y, and common mode signals. These signals are processed to form their absolute values, and are then summed to produce a voltage proportional to deviation of the direction of the eye from the desired axis. This voltage signal is compared with a background illumination signal by an adjustable threshold detector, which actuates a Schmitt trigger to indicate deviation of the attention of the eye.

7 Claims, 6 Drawing Figures

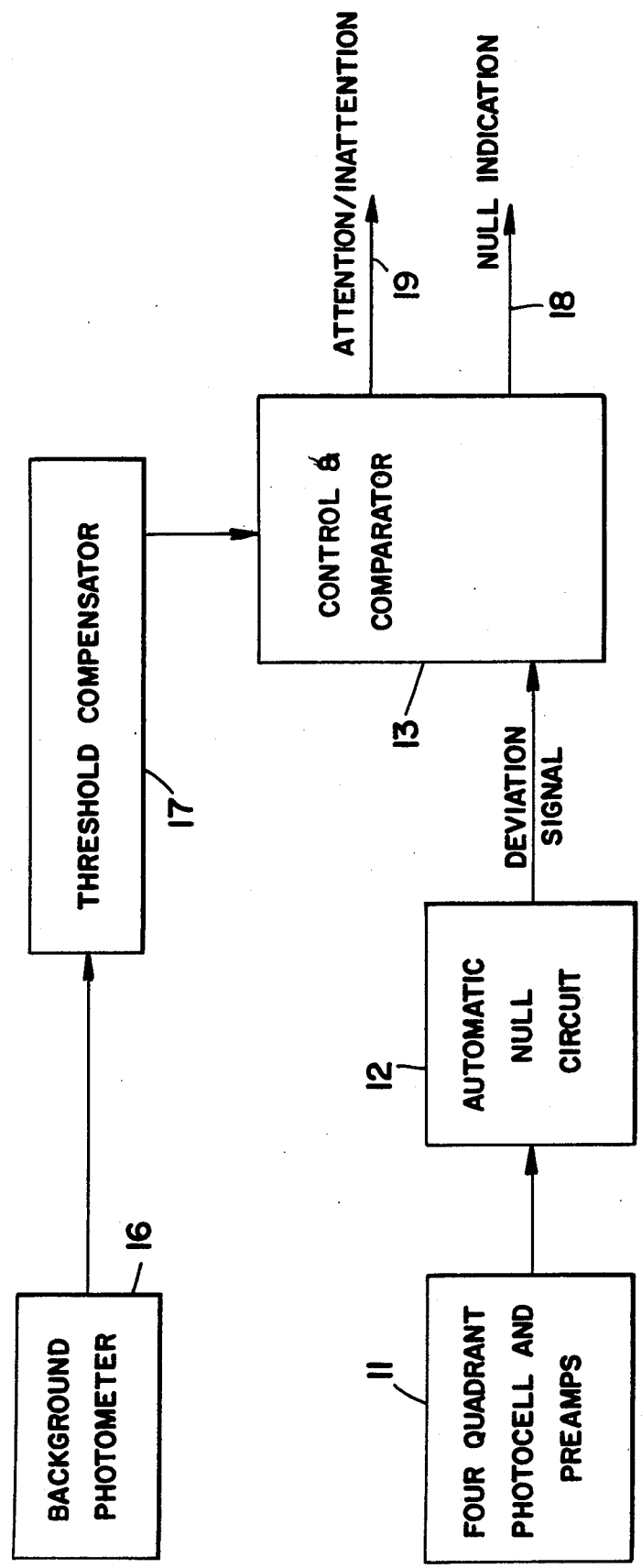
FIG_1

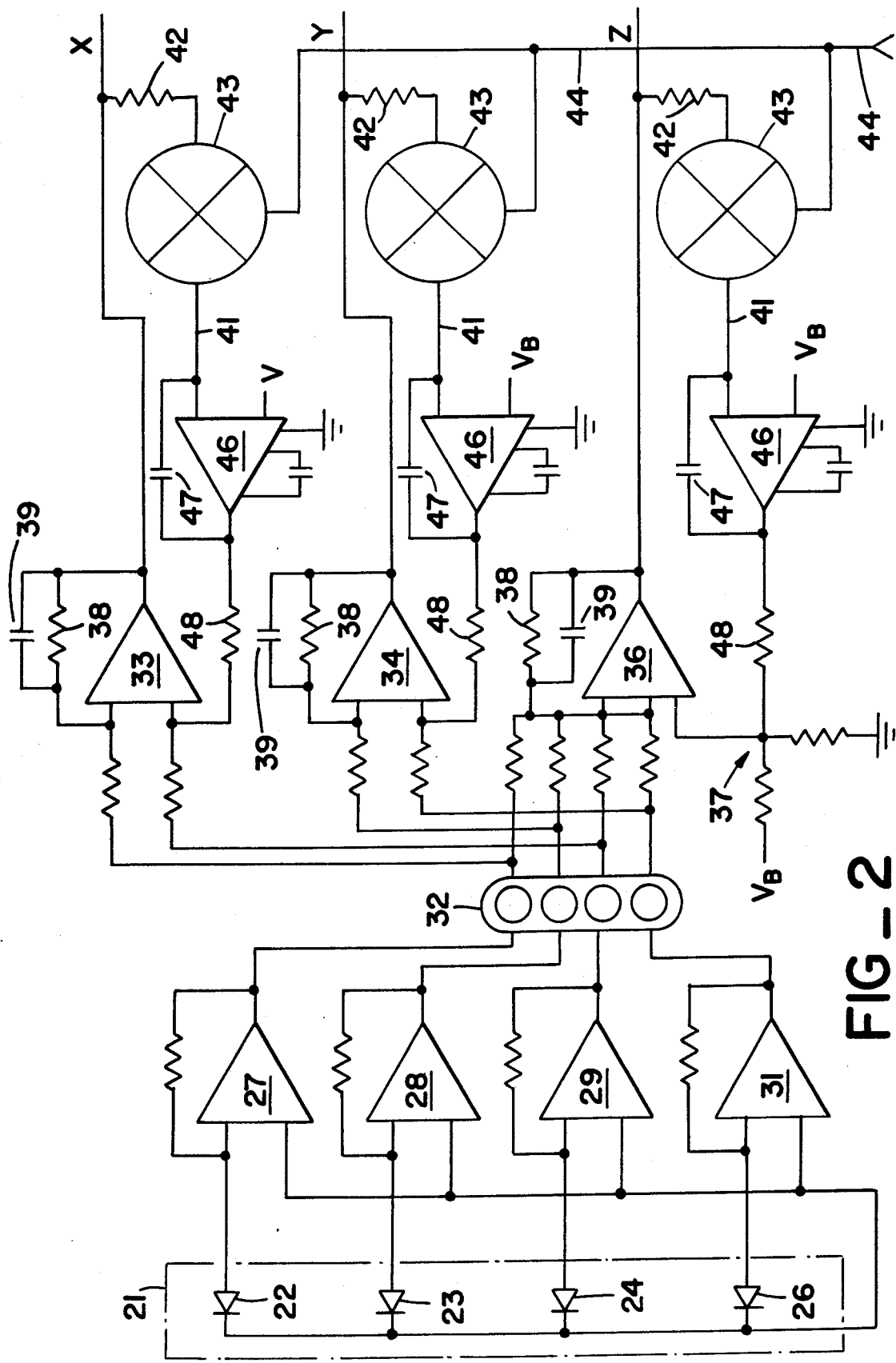
FIG_2

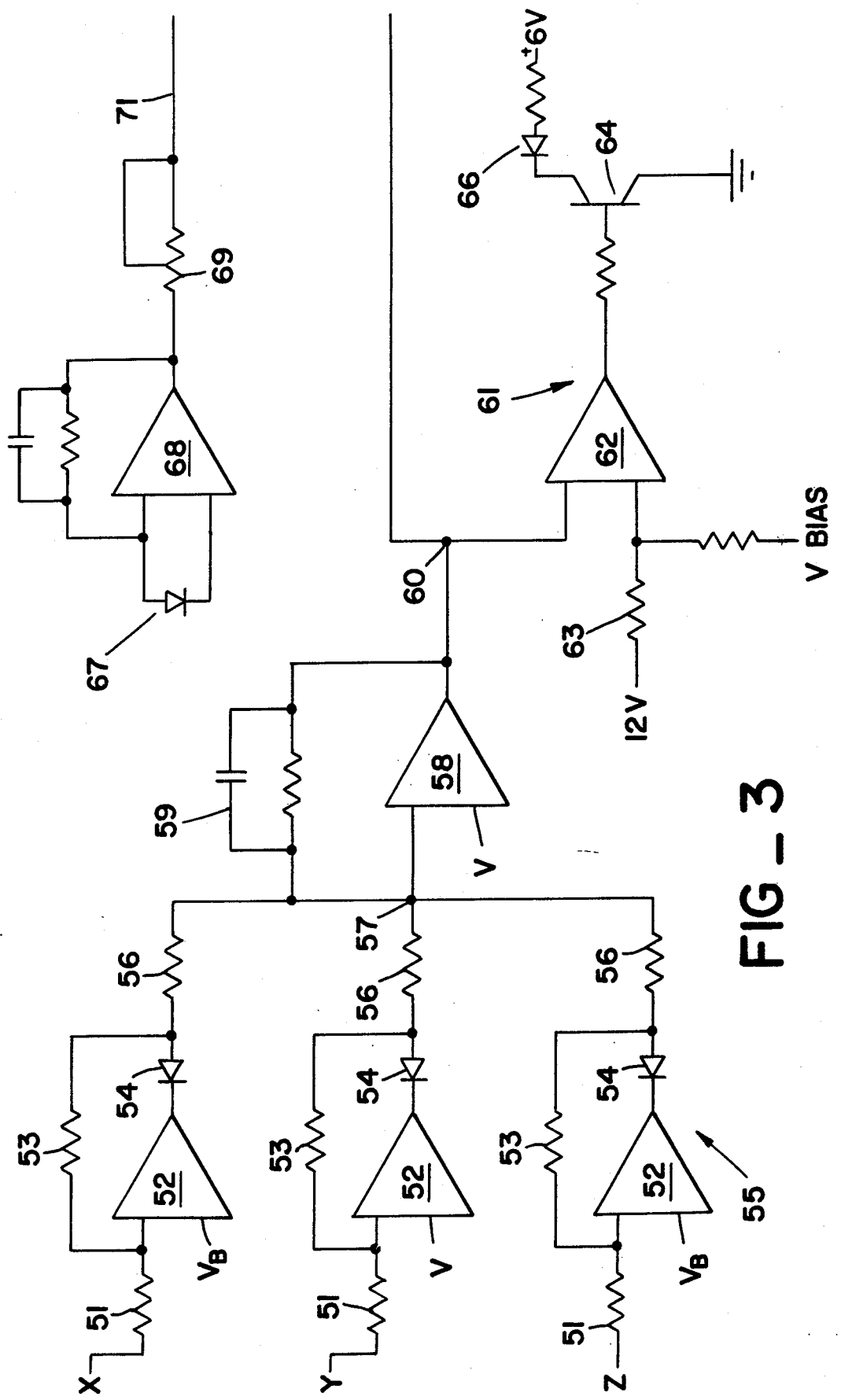
FIG_3

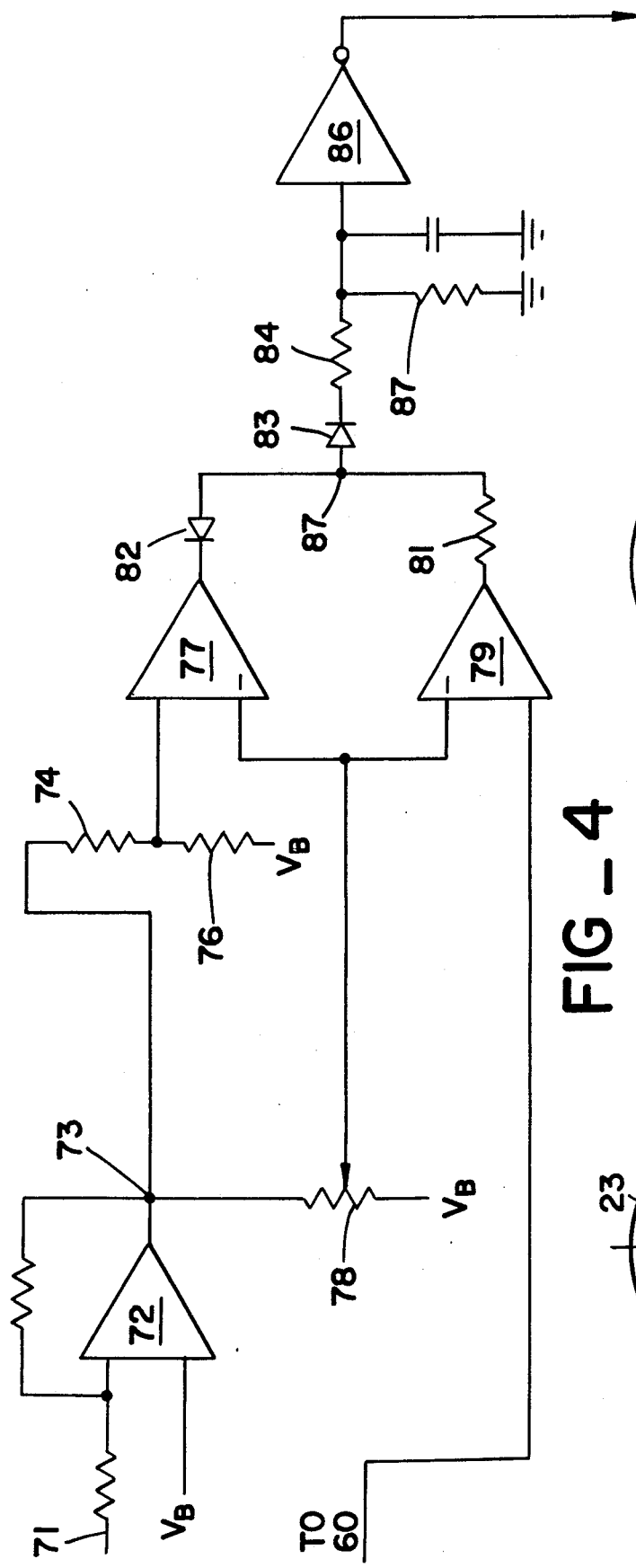
FIG_4
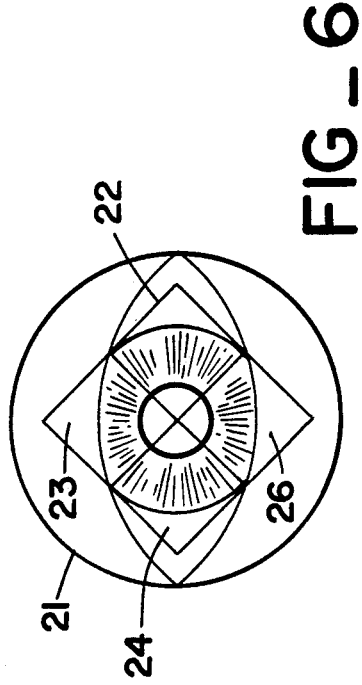
FIG_6
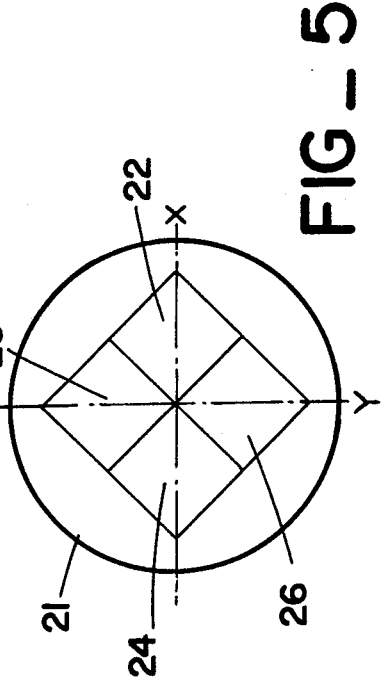
FIG_5

EYE ATTENTION MONITOR

BACKGROUND OF THE INVENTION

The following U.S. Pat. Nos. are the most pertinent prior art known to the inventor: 3,583,794, 3,598,107, 3,679,295, 3,832,066.

The present invention generally relates to a device for sensing any movement of an image falling on a photodetector. One important use for such a device is to determine the deviation of the fixation of an eye from a particular point or axis. There are many devices known in the prior art for accomplishing such a task. The most basic one comprises a photodetector on which the image of the eye falls, and a circuit for sensing the change in output of the photodetector which is commensurate with movement of the eye. This sort of device is sensitive only to gross eye movement.

Other prior art devices employ a plurality of photocells, arrayed in pairs and directed to diametrically opposed portions of the limbus of the eye. These systems have a major drawback in that the photocells must be individually directed to the correct portions of the limbus, a process which is time consuming and painstaking. Each photocell requires a separate optical system, thus greatly increasing the cost of the overall system. Furthermore, these types of prior art devices are not adept at sensing blinking of the eyelids, squinting of the eye, or the like. Similar devices, using infrared illumination of the eye, suffer from similar disadvantages.

There are also various ways known in the prior art for processing the signal from the photo detectors. Aside from threshold detectors mentioned in the foregoing, the sum devices have used sample and hold techniques to compare the photodetector signal at any given time with the signal level held from a previous time. A threshold detector is then utilized to sense any differences between the current signal and the held signal, so that significant changes indicative of eye movement may be sensed. These devices are driven by a digital clock to re-sample the signal periodically and update the comparison with the held signal. This form of signal processing has not proven itself to be well suited to sensing small deviations in eye fixation.

SUMMARY OF THE PRESENT INVENTION

The present invention generally comprises a device for sensing movement of an image of an eye falling on a four quadrant photocell detector. The signals from each quadrant of the detector are buffered by preamplifiers, and are fed to a plurality of differential amplifiers. The signals from the first and third quadrants are summed by one differential amplifier, while the signals from the second and fourth quadrants are summed by another differential amplifier. A third differential amplifier is used to add all of the signals from the four quadrants together. A separate integrating feed-back loop is selectively coupled to each differential amplifier to establish an initial comparison voltage in a storage capacitor in the feedback loop. Whenever the inputs to any differential amplifier differ from the voltage stored in the associated capacitor, the differential amplifier will respond by changing its output voltage level.

The three output signals coming from the three differential amplifiers, which represent the X quadrants, Y quadrants, and summed quadrants, are fed through operational amplifiers which are arranged to provide the absolute value of the input signal. The three absolute value signals are then summed by another amplifier to produce an average eye attention signal.

The invention also includes a photodetector for sensing the background illumination which is falling on the eye itself. This signal is processed so that the voltage of the background signal is directly related to background illumination. The average attention signal is compared with a selectively variable portion of the background voltage signal by a differential amplifier. Should either the average eye attention signal change, indicative of eye movement in the X or Y directions or blinking, or the background voltage signal change, indicative of sudden change in illumination of the eye or illumination of the target to which the eye is directed, the differential amplifier will produce an output signal which actuates a Schmitt trigger. The Schmitt trigger signal can then be used to actuate an indicator showing eye movement, or may be used to control eye testing apparatus.

A BRIEF DESCRIPTION OF THE DRAWINGS

FIG. 1 is a block diagram of the circuitry of the present invention.

FIG. 2 is a schematic representation of a portion of the circuitry of the present invention.

FIG. 3 is a schematic representation of another portion of the circuitry of the present invention.

FIG. 4 is a schematic representation of a further portion of the circuitry of the present invention.

FIG. 5 is a schematic representation of a four quadrant photocell detector.

FIG. 6 is a schematic representation of a four quadrant detector, as shown in FIG. 5, with an image of an eye falling thereon.

DESCRIPTION OF THE PREFERRED EMBODIMENT

The present invention generally comprises a device for sensing the movement of an object by detecting a shift in the image of the object which falls on a four quadrant photocell detector. Although the preferred embodiment relates to the sensing of the deviation of the fixation of an eye from a desired point or axis, it should be noted that the scope of the invention is not limited to such use.

As shown in FIG. 5, a four quadrant photocell detector 21 includes four adjacent light sensing surfaces 22, 23, 24, and 26. The light sensing portions 22 and 24 are disposed along the X axis, while the light sensing surfaces 23 and 26 are disposed along the Y axis. As shown in FIG. 6, the image of the eye which is being monitored to sense deviation of the eye from a desired fixation falls on the detector 21 so that the longitudinal extent of the image is generally coincident with the X axis of the photodetector. Furthermore, the center of the image of the pupil is coincident with the intersection of the X and Y axes of the photodetector.

As shown in FIG. 1, the four quadrant photocell detector and the associated preamplifiers 11 put out signals indicative of the light intensity falling on each quadrant of the detector. These signals are conducted to an automatic null circuit 12. The automatic null circuit sums the signals from the quadrants on the X axis, and also sums from the quadrants on the Y axis. Furthermore, it sums all of the quadrants to produce a common mode signal. These three signals are processed to form the absolute value of each, and these absolute values are summed to produce a positive voltage proportional to the deviation of the image intensity from a predetermined null condition. The predetermined null condition is also set as a stored voltage level by the automatic null circuit.

The deviation signal from the automatic null circuit is received by a control and comparitor circuit 13. The invention also includes a background photometer 16 which produces a voltage analogous to the background illumination which is falling on the eye being observed. The signal from the background photometer 16 is amplified by a threshold compensator 17 to provide a fixed relationship between background illumination signal voltage level and the actual background illumination. This signal is also received by the control and comparitor circuit 13.

The circuit 13 compares a portion of the voltage signal from the threshold compensator 17 with the deviation signal from the automatic null circuit 12. If these two signals should diverge beyond a predetermined tolerance, the control and comparitor circuit actuates a Schmitt trigger which produces an output signal on line 19 indicative of the fact that the image of the eye has wandered from its original position on the photocell detector 21. The control and comparitor circuit 13 also provides a circuit for indicating that the automatic null circuit 12 had achieved an initial null condition when the circuitry of the invention is initially set up for monitoring eye fixation. This null indication is provided on line 18, and may also include a visual or audible signal.

As shown in schematic diagram of FIG. 2, the four sensing portions 22, 23, 24, and 26, of the four quadrant photocell detector 21, are each connected to respective preamplifiers 27, 28, 29, and 31. Each preamplifier converts the current signal from its associated photosensing portion to a voltage signal, and conducts that voltage signal to a connecting block 32.

The circuitry includes a trio of differential amplifiers 33, 34, and 36 which are connected to the block 32 to operate on the signals from the preamplifiers. The differential amplifier 33 is connected to the signals from the quadrant detectors 22 and 24 while the differential amplifier 34 is connected to the signals coming from the quadrant sensing portions 23 and 26. The differential amplifier 36 is connected to all four sensing portions of the photocell detector. It should be noted that each differential amplifier effectively subtracts the two inputs thereto, amplifying the difference between the two signal inputs. The differential amplifier 36 adds all four signals to form the negative input thereto, while the positive input is provided by a voltage divider network 37. Each of the differential amplifiers 33, 34, and 36 is provided with a feedback loop control comprising a large resistance 38 and a small capacitance 39 connected between the output of each differential amplifiers and the negative input thereof.

Each differential amplifier 33, 34, and 36 is also provided with an null set feedback loop 41, which is selectively connected between the output and the positive input of each of the differential amplifiers. Each feedback loop 41 includes a limiting resistor 42, and a solid state switch 43, all of the switches 43 being actuated by a control signal provided through conductor 44. Each feedback loop also includes a differential amplifier 46, the feedback signal being connected to the negative input thereof and the positive input being connected to a biasing voltage $V_b$. A large capacitance 47 is also connected between the negative input and the output of each amplifier 46. The output of the differential amplifier is connected through limiting resistor 48 to the positive input of respective amplifier 33, 34, and 36.

Each feedback loop 41 is employed to establish a null voltage when the four quardant detector is initially directed at an image such as the image of the eye. An actuating voltage is applied to line 44 to complete each feedback loop. Each feedback loop intergrates the voltage emanating from its respective amplifier 33, 34, or 36, and the integrated voltage is stored by the large capacitor 47. A voltage on capacitor 47 quickly reaches a steady state, and this steady state voltage comprises the null level for each of the amplifiers 33, 34, and 36. Thereafter the signal on line 44 is discontinued, but the voltage on each capacitor 47 is applied to its respective amplifier. This voltage is maintained for some time as the capacitor 39 loses less than one millivolt per minute of operation.

It may be appreciated that the output of amplifier 33 is representative of changes in the illumination of the X quadrant portions of the photosensor with respect to the stored voltage of the respective capacitor 47; thus the output of amplifier 33 is termed the X output. Likewise the output of the amplifier 34 is the Y output and the output of amplifier 36 is the Z output. Variations in the X output correspond to the motion of the eye image along the X axis, while variations in the Y output correspond to motion of the eye image along the Y axis. The variations in the Z output correspond to changes in all four quadrants of the photodetector. Such changes are usually occasioned by blinking or squinting of the eye.

The X, Y, and Z signals are then fed to an absolute value circuit 55. Each signal is fed to a respective differential amplifier 52 through a limiting resistor 51. The output of each differential amplifier 52 is connected to a diode 54, and a feedback loop comprising a resistor 53 is connected from the anode of each diode to the negative input of the differential amplifier 52. The anode of each diode 54 is also connected through a large dropping resistor 56 to a common circuit node 57. The orientation of the diode 54 and the connection of the feedback loop functions to create the absolute value of the individual X, or Y, and Z signals, as is well known in the art. These signals are summed at the circuit node 57.

Differential amplifier 58 is connected to the node 57 to amplify the summed absolute values of X, Y, and Z signals. An RC feedback loop 59 is connected across the output and input of the amplifier 58. The output of the amplifier 58, which is connected to circuit node 60, is the average eye attention signal. Any fluctuation in this signal is due to a deviation of one of the photosensor signals from the initial null voltage level and is indicative of movement of the eye image in the X or Y direction, or blinking or squinting of the eye.

The average eye attention signal is fed to a null check circuit 61, which includes a differential amplifier 62. The other input of the amplifier 62 is a small positive voltage provided through a voltage divider network 63. The difference between the small positive voltage and the average eye attention signal is amplified by the amplifier 62 and fed to a transistor 64 which drives an LED null indicator 66. The null checking circuit 61 thus indicates that the average eye attention signal has obtained a minimum threshold voltage to actuate the LED indicator. This is important during the initial null setting procedure since actuation of the LED null indicator 66 indicates that the automatic null circuitry is functioning properly.

The background photometer 16 shown in FIG. 1 includes a photocell 67, shown in FIG. 3, which is oriented to receive the same background illumination as the eye which is forming the image falling on the four quadrant photodetector 21. The signal from photocell 67 is amplified by differential amplifier 68, the output of which is connected through a gain adjusting variable resistor 69 to conductor 71. As shown in FIG. 4, connector 71 is connected through a limiting resistor to another stage of differential amplification 72. The gain adjustment 69 and the value of the other components are chosen so that the output of differential amplifier 72, at node 73, is related to the background illumination by a known proportion. That is, at node 73 ten millivolts signal level is exactly equal to one Apostilb of background illumination. Thus the signal of node 73 is the background voltage signal.

The invention also includes a pair of differential amplifiers 77 and 79, each of which has its negative input connected to a potentiometer 78 which applies a selectively variable portion of the background voltage signal thereto. The other input of the differential amplifier 79 is connected to node 60, which supplies the average eye attention signal to the amplifier 79. Should the average eye attention signal from node 60 exceed a threshold level which is set by the potentiometer 78, the differential amplifier 79 will provide an actuating signal through resistor 81, diode 83, and resistor 84 to a Schmitt trigger 86. A parallel RC time delay network 87 is connected between the resistor 84 and the Schmitt trigger 86 to provide a slight time delay in the actuation of the Schmitt trigger. The output of the Schmitt trigger is indicative of a change in illumination of the four quadrant photocell detector greater than the threshold level set by potentiometer 78, and may be used to interrupt a testing procedure or actuate other instruments.

The differential amplifier 77 has its positive input connected to a voltage divider formed of resistors 74 and 76. This voltage divider is connected to node 73, and the values of resistors 74 and 76 are chosen so that approximately five percent (5%) of the voltage present at node 73 is applied to the positive input of differential amplifier 77.

The differential amplifier 77 thus compares the selectively variable portion of the background voltage signal provided by the potentiometer 78 with the fixed portion of the background voltage signal provided by the resistive network 74 and 76. Should the setting of the potentiometer 78 be within five percent (5%) of the minimum possible setting, the differential amplifier 77 will turn off. This action causes the junction 87, to which the output of differential amplifier 79 is connected, to be held close to ground potential by the deactuation of differential amplifier 77. In this situation, even though the differential amplifier 77 may provide an output indicative of inattention, the differential amplifier 77 will prevent actuation of the Schmitt trigger circuit 86. Thus, at low sensitivity settings of the potentiometer 78 the output of the Schmitt trigger 86 is effectively turned off.

It should be noted that the differential amplifier 79 compares the average eye attention signal with the selected portion of the background voltage signal provided by the potentiometer 78. Should the background illumination increase, the average eye attention signal would likewise increase, due to the initial null levels set by the capacitors 47 in the automatic null circuit. However, since both signals would increase to approximately the same extent, the Schmitt trigger 86 would not be actuated by the comparative output of the differential amplifier 79.

It has been found that the arrangement of the circuitry of the present invention provides extreme sensitivity to movement of the image on the four quadrant photocell detector, as well as great range in threshold sensitivity to angular deviation of the eye image from the center of the four quadrant detector. In the preferred embodiment, adjustment of the potentiometer 78 can vary the threshold trigger range from 2½ degrees to 50 degrees, approximately, of deviation of the eye image from the center of the four quadrant detector.

I claim:

1. A device for monitoring the position of an image eye, comprising a multi-faceted photocell detector on which falls said image, first differential amplifier means connected to opposed facets of said photocell detector for amplifying the difference of the signals therefrom; second differential amplifier means connected to all of said facets of said photocell detector for summing all of the signals therefrom; automatic null circuit means associated with each of said first and second differential amplifier means for storing an initial output voltage level related to the position and intensity of said image, said automatic null circuit means providing a portion of the input to said first and second differential amplifier means; means for generating absolute value signals from the output of said first and second differential amplifier means; means for summing said absolute value signals to form an average eye attention signal; third differential amplifier means for amplifying the difference between said average eye attention signal and a selectively variable voltage; and threshold detector means connected to the output of said third differential amplifier means for generating an output control signal.

2. The device of claim 1, further including a background illumination photometer for generating a voltage analog signal of the level of illumination of said object, said voltage analog signal comprising the voltage source of said selectively variable voltage.

3. The device of claim 1, wherein said multi-faceted photocell detector comprises a four quadrant photocell detector.

4. The device of claim 3, wherein said first differential amplifier means includes a pair of differential amplifiers, each connected to the signals from an opposed pair of quadrants of said photocell detector.

5. The device of claim 1, wherein said automatic null circuit means includes feedback loop means associated with each of said first and second differential amplifier means.

6. The device of claim 5, wherein said feedback loop means includes a storage capacitor for storing said initial output voltage level, and a solid state switch for selectively connecting said feedback loop means to said first and second differential amplifier means.

7. The device of claim 1, further including automatic null circuit checking means, including a differential amplifier having one input connected to said average eye attention signal, the other input connected to a fixed bias voltage, and output thereof connected to an indicator circuit means.

* * * * *

UNITED STATES PATENT AND TRADEMARK OFFICE
CERTIFICATE OF CORRECTION

PATENT NO. : 4,169,663
DATED : October 2, 1979
INVENTOR(S) : William C. Murr

It is certified that error appears in the above-identified patent and that said Letters Patent are hereby corrected as shown below:

Column 6, line 42, "object" should read --- eye ---.

Signed and Sealed this

Fifteenth Day of January 1980

[SEAL]

Attest:

SIDNEY A. DIAMOND

Attesting Officer

Commissioner of Patents and Trademarks